(12) United States Patent
Kuster

(10) Patent No.: US 8,000,004 B2
(45) Date of Patent: Aug. 16, 2011

(54) MICROSCOPE WITH CENTERED ILLUMINATION

(75) Inventor: Manfred Kuster, Widnau (CH)

(73) Assignee: Leica Instruments (Singapore) Pte. Ltd., Singapore (SG)

( * ) Notice: Subject to any disclaimer, the term of this patent is extended or adjusted under 35 U.S.C. 154(b) by 0 days.

(21) Appl. No.: 12/145,868

(22) Filed: Jun. 25, 2008

(65) Prior Publication Data

US 2009/0002812 A1    Jan. 1, 2009

(30) Foreign Application Priority Data

Jun. 28, 2007  (DE) .......................... 10 2007 029 893

(51) Int. Cl.
G02B 21/06     (2006.01)
G02B 21/00     (2006.01)

(52) U.S. Cl. .................... 359/388; 359/368; 359/385

(58) Field of Classification Search ........... 359/368–390
See application file for complete search history.

(56) References Cited

U.S. PATENT DOCUMENTS

| | | | |
|---|---|---|---|
| 5,748,367 A * | 5/1998 | Lucke et al. ................ | 359/385 |
| 6,473,229 B2 | 10/2002 | Nakamura | |
| 6,972,900 B2 * | 12/2005 | Sander ......................... | 359/372 |
| 7,102,818 B2 | 9/2006 | Sander | |
| 2001/0010592 A1 | 8/2001 | Nakamura | |
| 2003/0048530 A1 | 3/2003 | Sander | |
| 2004/0057108 A1 | 3/2004 | Namii | |
| 2004/0080816 A1* | 4/2004 | Koetke ....................... | 359/368 |

FOREIGN PATENT DOCUMENTS

| | | |
|---|---|---|
| DE | 195 23 712 C2 | 1/1996 |
| DE | 195 37 868 B4 | 4/1996 |
| DE | 101 44 062 A1 | 3/2003 |
| EP | 0 321 586 B2 | 6/1989 |
| EP | 1 424 582 B1 | 6/2004 |

OTHER PUBLICATIONS

Office Action issued by the United States Patent and Trademark Office for U.S. Appl. No. 12/145,863 dated Jun. 8, 2009.
Office Action issued by the United States Patent and Trademark Office for U.S. Appl. No. 12/145,863 dated Jan. 12, 2010.
Office Action issued by the United States Patent and Trademark Office for U.S. Appl. No. 12/145,863 dated Mar. 18, 2010.
Office Action issued by the United States Patent and Trademark Office for U.S. Appl. No. 12/145,863 dated Apr. 21, 2010.
Office Action issued by the United States Patent and Trademark Office for U.S. Appl. No. 12/145,863 dated Oct. 13, 2010.

* cited by examiner

Primary Examiner — Thong Nguyen
(74) Attorney, Agent, or Firm — Schlee IP International, P.C.; Alexander R. Schlee

(57) ABSTRACT

A microscope comprising a main objective having a variable focal length and comprising an illuminating unit including a light source and an illuminating optical system for generating an illuminating beam path directed onto the object plane and extending outside the main objective. A unit is provided for centering the illumination dependent on a variation of the focal length of the main objective, and the illuminating optical system is mounted at least in part in a laterally shiftable manner for centering the illumination. In particular, the illuminating optical system has a diaphragm that is mounted in a laterally shiftable manner.

10 Claims, 4 Drawing Sheets

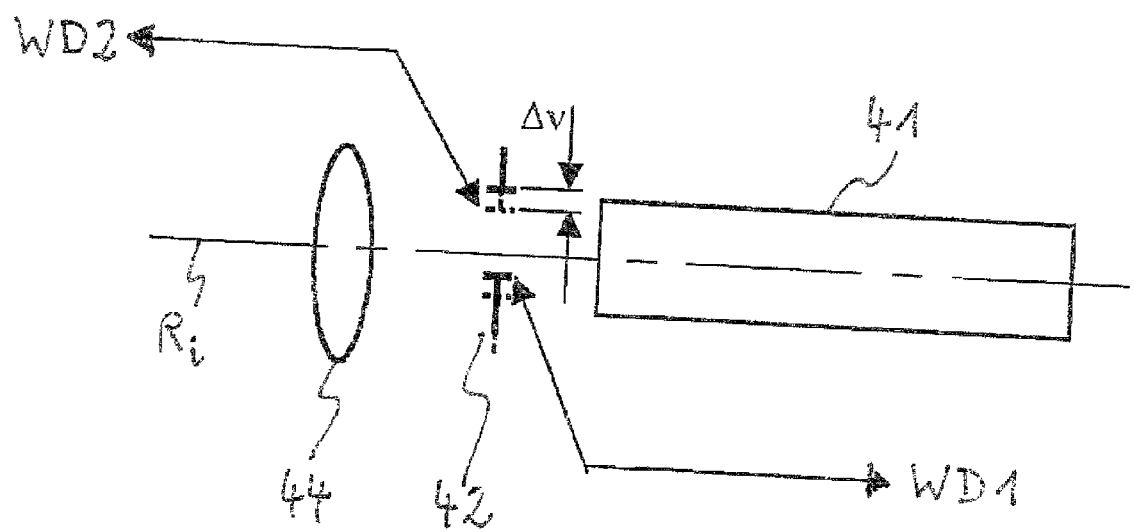

MICROSCOPE WITH CENTERED ILLUMINATION

This application claims the priority of the German patent application DE 10 2007 029 893.7 having a filing date of Jun. 28, 2007, the entire content of which is herewith incorporated by reference.

BACKGROUND OF THE INVENTION

The present invention relates to a microscope comprising a main objective having a variable focal length and comprising an illuminating unit including a light source and an illuminating optical system for generating an illuminating beam path directed onto an object plane and extending outside the main objective, means being provided for centering the illumination dependent on a variation of the focal length of the main objective.

Microscopes of this type are known from DE 195 23 712 C2 and DE 195 37 868 B4. In the first-mentioned DE 195 23 712 C2 a stereomicroscope comprising a main objective with variable focal length, a downstream zoom system and a binocular tube as well as an illuminating unit arranged adjacent to the main objective is disclosed. The main objective comprises a fixed and a movable lens for varying the focal length and the intercept length of the main objective. The fixed, negative lens of the main objective is arranged towards the object plane, the movable, positive lens is arranged behind it (facing away from the object plane). A movement of the movable lens in the direction away from the object plane results in a reduction of the focal length of the main objective. For an optimal illumination of the (shifted) object plane, it is suggested in this document to adjust the position of an illumination deflector element dependent on a focal length variation of the main objective for centering the illumination. This is done in that the prism lens used as an illumination deflector element is pivoted such that the illuminating beam path tracks the changed object position. For this purpose, the prism lens is pivotally mounted about an axis which is perpendicular to a plane that is spanned by the vertical optical axis of the main objective and the illuminating beam path which is incident substantially horizontally inclined on the prism lens. As a result thereof, for all positions of the movable lens of the main objective facing away from the object a focusing of the illuminating light on the respective focal point of the main objective can be guaranteed.

The coupling of the rotary movement of the illumination deflector element with the linear (vertical) movement of the lens of the main objective facing away from the object, as suggested in this document, requires very sensitive rotary movements of the illumination deflector element in relation to the movement of the lens and makes high demands on the mechanical coupling which is designed with a high constructional expense in this document. Any disturbances will be directly visible for the user (particularly given high magnifications). Further, the size of the surface of the deflector element turns out to be disadvantageous, as it has to be sufficiently large in order to cover the entire illuminating pencil even when the illumination deflector element is tilted. As illumination deflector elements, mirrors or the mentioned prism lenses can be used. When mirrors are used, an increase of the reflecting surface will result in the additional disadvantage of an increased required thickness of the reflecting surface. Thus, altogether the required space and the height of the weight to be moved are increased.

In the mentioned DE 195 37 868 B4, an illuminating device for a stereomicroscope comprising an objective with a variable image-forming intercept length is disclosed, an illumination intercept length variation being possible via an optical system that is separate from the viewing optical system. Means for coupling the intercept lengths mentioned are disclosed, which means effect that the illumination intercept length and the image-forming intercept length correspond to one another. Further, means for coupling are provided which guarantee that the angular position of a deflector element of the illuminating device is varied such dependent on the respective image-forming intercept length and illumination intercept length that there is always a centered illumination of the viewed field of view. Since, here too, for centering the illumination, rotary movements of the illumination deflector elements are performed, here, once again, the disadvantages mentioned occur.

A basically different possibility of illumination centering results when the illumination is guided through the main objective of the microscope. This solution is implemented in the surgical microscope models M520 and M525 of the applicant. Here, the illumination deflector element directs the illuminating beam path to and through the main objective having variable focal length so that the illumination is always centered on the focus.

An optical binocular viewing system comprising one main objective common for both channels and a viewing zoom system as well as an illuminating system having an illuminating zoom system is suggested in EP 0 321 586 B2. The illuminating beam path is guided through the main objective via a deflecting prism. The illuminating zoom system is adjusted dependent on the viewing zoom system in order to adapt the size of the illuminated field to the varying zoom magnification.

The microscopes mentioned up to now use vertical zoom systems, i.e. the longitudinal axis of the zoom system lies parallel to the optical axis of the main objective. If, in addition, the illumination is fed into the main objective from above, there will be a high space requirement in vertical direction resulting in microscopes having a relative high overall height in the vertical direction. This is disadvantageous for ergonomic reasons since the distance between the eyepiece and the main objective is increased.

From U.S. Pat. No. 6,473,229 B2, a stereomicroscope comprising a horizontally arranged illuminating unit is known, the illuminating beam path of which being directed via a fixed deflecting mirror outside the main objective onto the object plane. The stereomicroscope suggested therein has a main beam path and an assistant beam path, for each of the two beam paths separate optical systems comprising a lens system, a zoom system and a binocular tube being provided. While one of the zoom systems is designed such that is lies horizontally, the axis of the other zoom system is inclined to the vertical which is perpendicular to the object plane. Here, with respect to illumination centering given a variable focal length of one of the lens systems no suggestions are made.

For reducing the vertical constructional height, a stereomicroscope structure has been suggested in EP 1 424 582 B1, in which a "lying" zoom system, i.e. a zoom system having its longitudinal axis arranged horizontally, is realized. For this purpose, there is arranged between the main objective and the zoom system a deflector element which deflects the viewing beam path from a substantially vertical direction into a substantially horizontal direction and feeds the same to the zoom system arranged in a first horizontal plane. By means of further deflector elements the viewing beam path exiting the zoom system is deflected into a second horizontal plane which extends substantially parallel to the first horizontal plane and in which optical add-on components are arranged.

With respect to details on the structure and the mode of functioning of such a stereomicroscope with "lying" zoom system reference is explicitly made to the mentioned European patent specification.

In this stereomicroscope, the illuminating unit is arranged substantially adjacent to the main objective in horizontal direction und below the zoom system in vertical direction, the illuminating beam path being guided outside the main objective. Instead of an illumination centering, it can be ensured by means of a sufficiently large illuminated field that the visual field is always illuminated given a focal length variation of the main objective. Such a generously designed illuminated field requires a correspondingly largely designed illuminating unit which in turn has a negative effect on the ergonomics of the microscope. A further disadvantage is here that the homogeneity of the illumination (distribution of the illuminated field) cannot be the same for all positions of the multi-focus (variable focus lens). Only another part of the entire available illuminated field is used.

Finally from DE 101 44 062 A1 and the corresponding U.S. Pat. No. 7,102,818 B2 a stereomicroscope comprising an illuminating device is known, in which the illuminating beam path is faded into the main beam path of the microscope from a substantially horizontal direction via a deflecting mirror and is guided to the object via the main objective. The diameter of the deflecting mirror is here larger than the distance between the viewing beam paths (stereobasis) and it has free openings for the viewing beam paths. In addition, in the illuminating device suggested therein, a diaphragm is provided which can be radially shifted in the illuminating beam path, as a result whereof the angles of incidence of the light beams illuminating the object can be varied in radial direction (relative to the main beam path of the microscope). In this way, the object can be illuminated from various angles without the illuminated field being shifted laterally. Since the illuminating beam path is guided through the main objective in this document, the problems relating to the illumination centering is naturally not mentioned therein. A large illuminating aperture is required for the way of proceeding suggested herein (which, in practice is often not sufficiently present).

In addition, a tracking of the illuminated field with respect to position and size has the advantage that the diameter of the illuminated field can be kept at a minimum and be adapted to the field of view so that in the case of surgical microscopes the patient will be exposed to a minimum of radiation.

The present invention is to be particularly suitable for the illumination centering in a microscope structure making use of "lying" zoom systems.

SUMMARY OF THE INVENTION

The problem to be solved by the present invention is to realize in a technically easy way a centering of the illumination given a focal length variation of the main objective of the microscope.

The inventive microscope comprises a main objective having a variable focal length, for which, for example, a lens assembly movable in the direction of the optical axis of the main objective can be provided. In this application, the terms multi-focus or variable focus lens shall refer to such a main objective of variable focal length. Without restricting the generality, it is assumed in the following that this main objective comprises a fixed part facing away from the object and an object-facing movable part, each of these parts including a lens assembly. A lens assembly can comprise a single lens or a combination of lenses. The variable focus lens can also be constructed such that the lower, object-facing part is fixed, and the upper part, facing away from the object, is movably designed. By using such a variable focus lens different image planes can be focused in a certain area.

The inventive microscope further comprises an illuminating unit including a light source and an illuminating optical system for generating an illuminating beam path directed onto an object plane and extending outside the main objective.

According to the invention, the illuminating optical system is mounted at least partially laterally shiftably for centering the illumination dependent on a variation in focal length of the main objective. The term "laterally shiftably" means in this connection a shiftability not only in axial direction, i.e. not exclusively in the direction of the illuminating axis, but in a direction inclined thereto or perpendicular thereto so that, consequently, an additional shifting component in axial direction shall not be excluded. It turned out that by means of such a lateral shifting of at least a part of the illuminating optical system, the illuminating focus can technically easily and reliably tracked to the focus of the main objective. Further, it turned out that it is sufficient to design only part of the illuminating optical system laterally shiftably. This is advantageous since in this way not the entire illuminating unit has to be mounted shiftably but only a part of the actual illuminating optical system.

DETAILED DESCRIPTION OF THE INVENTION

In the microscope according to the invention, the illuminating optical system advantageously has a laterally shiftably mounted diaphragm. This diaphragm can in particular be a field diaphragm often used in the illuminating units considered herein.

An illuminating unit used for the invention advantageously has, as seen from the light source, as an illuminating optical system a collector, a diaphragm as well as an illuminating lens assembly for focusing the illuminating beam path into the object plane. The opening of the diaphragm, often an iris diaphragm having a variable diameter, is imaged via the lens assembly on the object plane given Köhler illumination. Other types of illumination as well as illumination units structured otherwise can be used. An illumination deflector element can be arranged upstream or preferably downstream of the illumination lens assembly. As a result thereof, it is in particular possible to use an illuminating unit arranged at least partially horizontally and to deflect the generated illuminating beam path by means of the illumination deflector element in a vertical direction in the direction of the object plane. The illumination lens assembly can in principle represent a single lens or a combination of lenses.

As mentioned, the illuminating unit is often at least partially arranged such that the generated illuminating beam path is incident on the illumination deflector element in a direction that is substantially perpendicular (or inclined) to the optical axis of the main objective, which, without restricting the generality, is substantially vertically directed ("horizontal illuminating unit"). The illumination deflector element deflects this illuminating beam path then in the direction of the object plane on the focus of the main objective. This section of the deflected illumination beam path encloses a specific angle with the vertical (normal to the object plane). Given a variation of the focal length of the main objective which results in a shifting of the imaged object plane in vertical direction given this arrangement, this angle likewise has to be varied so that the illumination remains centered. Surprisingly, it turned out that this variation of said angle can simply be effected by a lateral shifting of the diaphragm of the illuminating optical system, in particular the field diaphragm, even given a stationary illumination deflector element. As a result of this shifting one obtains a laterally shifted illuminated field that can be centered on the field of view. In particular, a linear shifting of the diaphragm is sufficient and this shifting can take place in particular perpendicular to the illuminating axis.

In principle, also other lateral shiftings are conceivable, for example shiftings which are inclined to the illuminating axis, i.e. with an additional axial component, or shiftings along a curved path. Given the mentioned Köhler illumination, the iris diaphragm is imaged on the object plane. Given a variation of the working distance or, respectively, the focal length of the main objective, there results a corresponding shifting of the object plane along the optical axis of the main objective so that the iris diaphragm is imaged out of focus on the shifted object plane. This effect can be compensated in that the iris diaphragm is additionally shifted in axial direction, i.e. along the illuminating axis, in order to obtain an imaging of the iris diaphragm in the new (shifted) object plane with edge sharpness. Given this way of proceeding, to each lateral shift of the iris diaphragm (perpendicular to the illuminating axis) a corresponding axial shift of this iris diaphragm (in the direction of the illuminating axis) can be assigned in order to obtain a centered and sharp imaging of the iris diaphragm in the respective object plane.

It is expedient if a control unit for coupling a variation of the focal length of the main objective with an amount of lateral shift of the at least one part of the illuminating optical system is provided. Here, it is useful, with respect to the specific microscope structure comprising the specific illuminating unit, to assign at least for a number of working distances (or, respectively, focal lengths of the main objective) the correspondingly necessary lateral shift amounts and to derive a corresponding relationship therefrom (numerical or in the form of a formula), which is afterwards entered into a corresponding control. The mentioned relationship can also be established with the aid of suitable software by ray tracing given different working distances and a best-fit method. A closed loop control of the illumination centering can also be considered.

It is noted that the features of the invention which have already been mentioned and which are still to be mentioned cannot be used only in the combination given herein but, as far as technically useful, also alone or in other combinations, without leaving the scope of the present invention.

In the following, an embodiment illustrated schematically in the drawing shall explain the invention and its advantages in more detail.

BRIEF DESCRIPTION OF THE DRAWINGS

FIG. 4 shows in detail a cutout of FIG. 3 for further illustration of the invention.

DETAILED DESCRIPTION OF THE DRAWINGS

Figure 1:
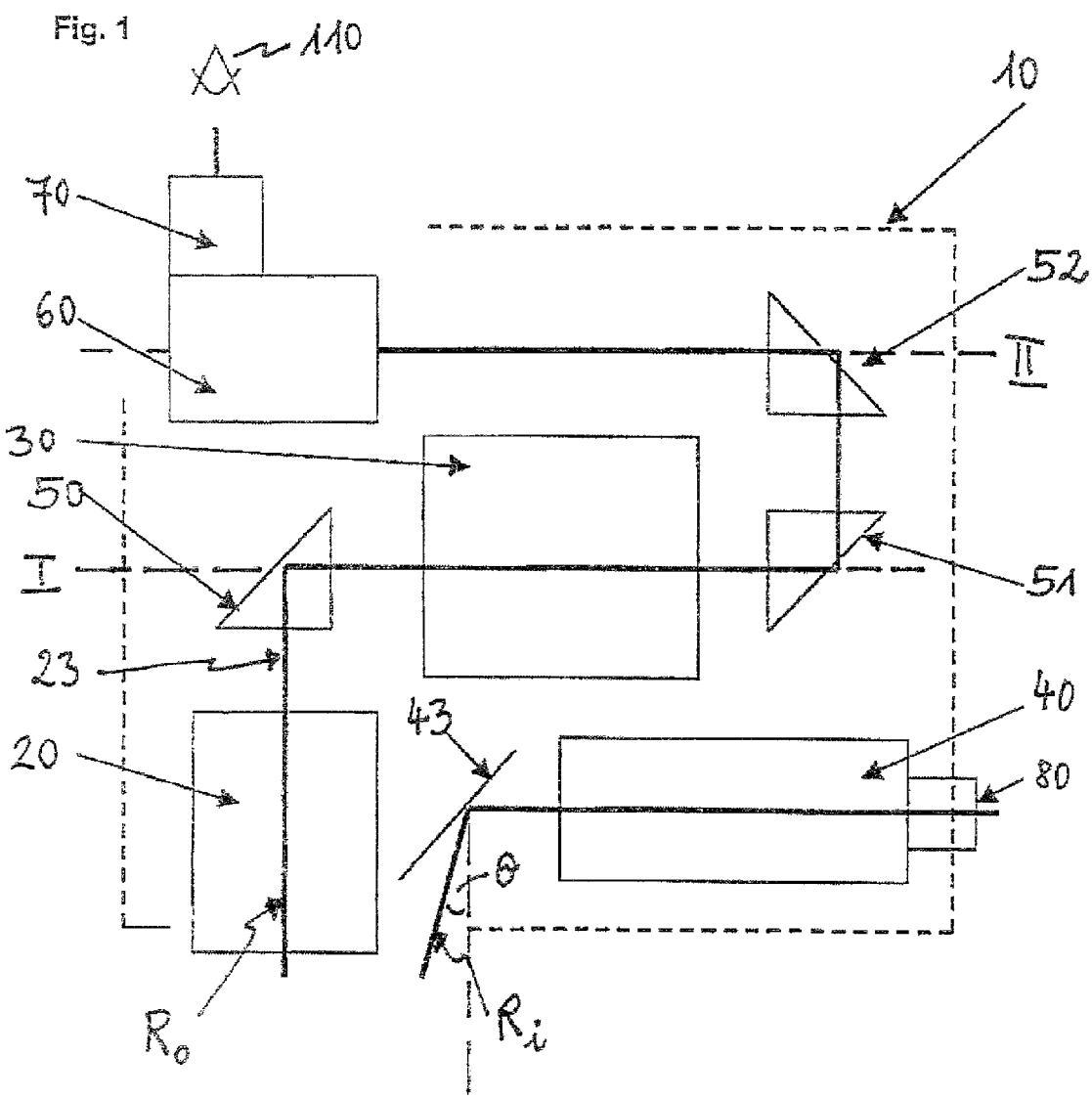
FIG. 1 schematically shows the structure of a microscope with which the invention can preferably be used.

FIG. 1 very schematically shows the basic structure of a microscope 10, here designed as a surgical stereomicroscope, for a better illustration only the viewing axis $R_o$ being illustrated. Such surgical microscopes often have an additional pair of viewing beam paths for assistant's viewing in addition to a pair of main viewing beam paths. Microscopes of this type are known per se and therefore are not to be explained in more detail here. In this connection, reference is made to the stereomicroscope described in the already mentioned EP 1 424 582 B1 in which, as in the present case, a "lying" zoom system 30 is realized.

The surgical microscope 10 comprises a main objective 20 which is designed as a multi-focus (or variable focus lens), i.e. represents a lens having a variable focal length. The main objective 20 defines an optical axis 23 which is perpendicular to an object plane 100. By varying the focal length of the main objective 20, focusing on the respective object plane 100 can be effected. The viewing beam paths run parallel to the shown optical axis 23 and lie, for example, either in the drawing plane or in a plane perpendicular to the drawing plane and including the optical axis 23. For deflecting the viewing beam paths a first deflector element 50 is arranged in the beam path and deflects the viewing beam paths from a substantially vertical direction into a substantially horizontal direction into the "lying" zoom system 30. The zoom system 30 is arranged with its longitudinal axis in a first horizontal plane I. Instead of a zoom system 30 which serves for the continuous magnification of the object image a discretely operating magnification changer can likewise be provided. By means of further deflector elements 51 and 52, the viewing beam path is directed into a second horizontal plane II. Here, the tube 60 is arranged, which directs the illuminating beam path into at least one eyepiece 70 through which an observer 110 can view the microscope image. The principle structure of the described microscope components such as main objective, zoom system, tube and eyepiece is common to the person skilled in the art. In the beam path illustrated in FIG. 1, optical add-on components such as filters, image inverters, components for extending the optical path length, optical beam splitters for assistant's viewing, etc. can be arranged. Finally, between the zoom system 30 and the tube 60 an output (optical/mechanical) for documentation (camera, video, etc.) can be present.

An illuminating unit 40 connected to a light guide 80 can be arranged ergonomically favorable with its longitudinal axis substantially horizontally below the zoom system 30 so that it serves for the illumination of the object. What is illustrated here is a fiber illumination via an optical fiber. However, a direct halogen, xenon or LED illumination can likewise be used. The illuminating beam path generated by the illuminating unit 40 and illustrated by means of its illuminating axis $R_i$ is directed by means of an illumination deflector mirror 43 in the direction of the object plane 100. As can be taken from FIG. 1, the illuminating beam path is guided outside the main objective 20 of the microscope 10. Therefore, given a focal length variation of the main objective 20 resulting in a shift of the object plane 100 in vertical direction (variation of the working distance), the illuminating beam path has to be tracked for an optimal illumination. As can be taken from FIG. 1, the axis $R_i$ of the illuminating beam path encloses the angle θ with the axis $R_o$ of the viewing beam path, which angle θ is to be tracked given a variation of the working distance. The inventive type of this tracking of the illumination shall be explained in more detail with reference to the following figures.

Figure 2:
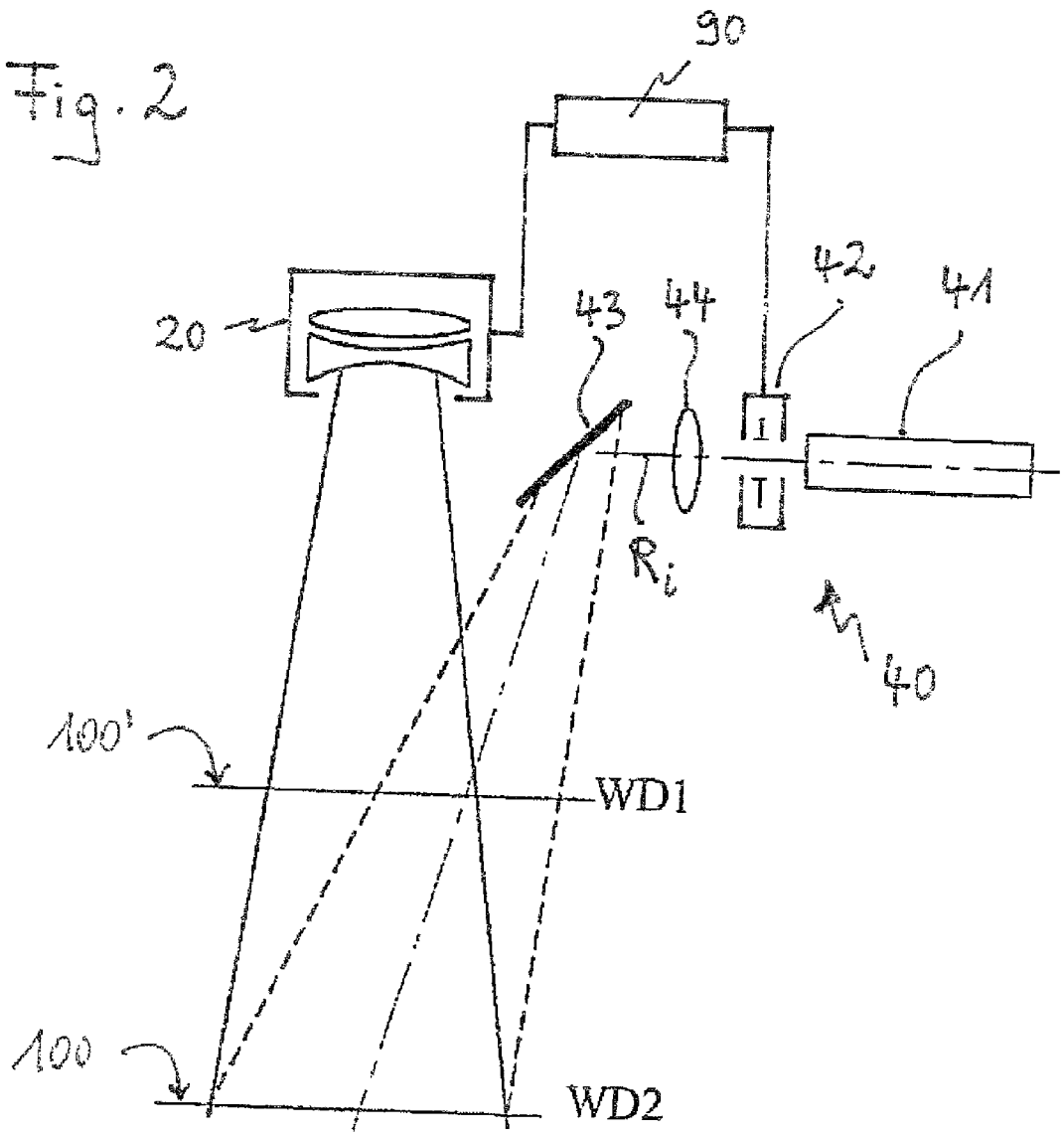
FIG. 2 schematically shows the illumination of the object plane given a first working distance, i.e. a first focal length of the main objective of the microscope.

FIG. 2 shows a schematic cutout of the inventive microscope in a particular embodiment. In FIG. 2, the structure of an illuminating unit 40 is illustrated, as to be preferably used for the present invention. The collector (here with the light source) is referenced 41. The collector 41 collects the light from the light source and images the same via the diaphragm 42 and the illuminating lens assembly 44 on the object plane 100. The diaphragm 42 is preferably an iris diaphragm having a variable diameter in the function of a field diaphragm.

As can be taken from FIG. 2, the axis of the viewing beam path, i.e. the optical axis of the main objective 20, is perpendicular to the object plane 100. The illuminating unit 40 at first generates an illuminating beam path having the axis $R_i$ and directed substantially perpendicularly to the optical axis of the main objective 20 ("horizontal illuminating unit"). By means of an illumination deflector element 43, this illuminating beam path is directed in the direction of the object plane 100. A plane mirror or also a spherical mirror can be used as an illumination deflector element 43. The illumination lens assembly 44, which is usually a lens group having a variable illumination intercept length, can be arranged upstream or downstream of the illumination deflector element 43 as viewed from the light source. Given a multi-membered structure of the lens assembly 44, also a partial arrangement upstream and downstream of the illumination deflector element 43 is conceivable.

The focal length of the main objective 20 of the microscope 10 (see FIG. 1) as illustrated in FIG. 2 is adjusted such that the focus lies in the object plane 100 which has the working distance WD2 with respect to the objective 20. Without restricting the generality, it is assumed that the field diaphragm 42 is in a central position, i.e. the geometric center of the field diaphragm 42 lies on the illuminating axis $R_i$ of the illuminating beam path. It can be taken from FIG. 2, that given this arrangement the illuminated field on the object plane 100 with the working distance WD2 optimally coincides with the field of view, as determined by the focal length of the main objective 20, i.e. with respect to position and size both fields optimally correspond to one another. In this connection, it is noted that certain cases are conceivable, in particular in the surgical microscopy, in which a larger illuminated field is desired in order to better illuminate a surgical area. Without restricting the generality, in the following however a coupling of the illuminated field with the visual field or field of view as exactly as possible shall be assumed.

Figure 3:
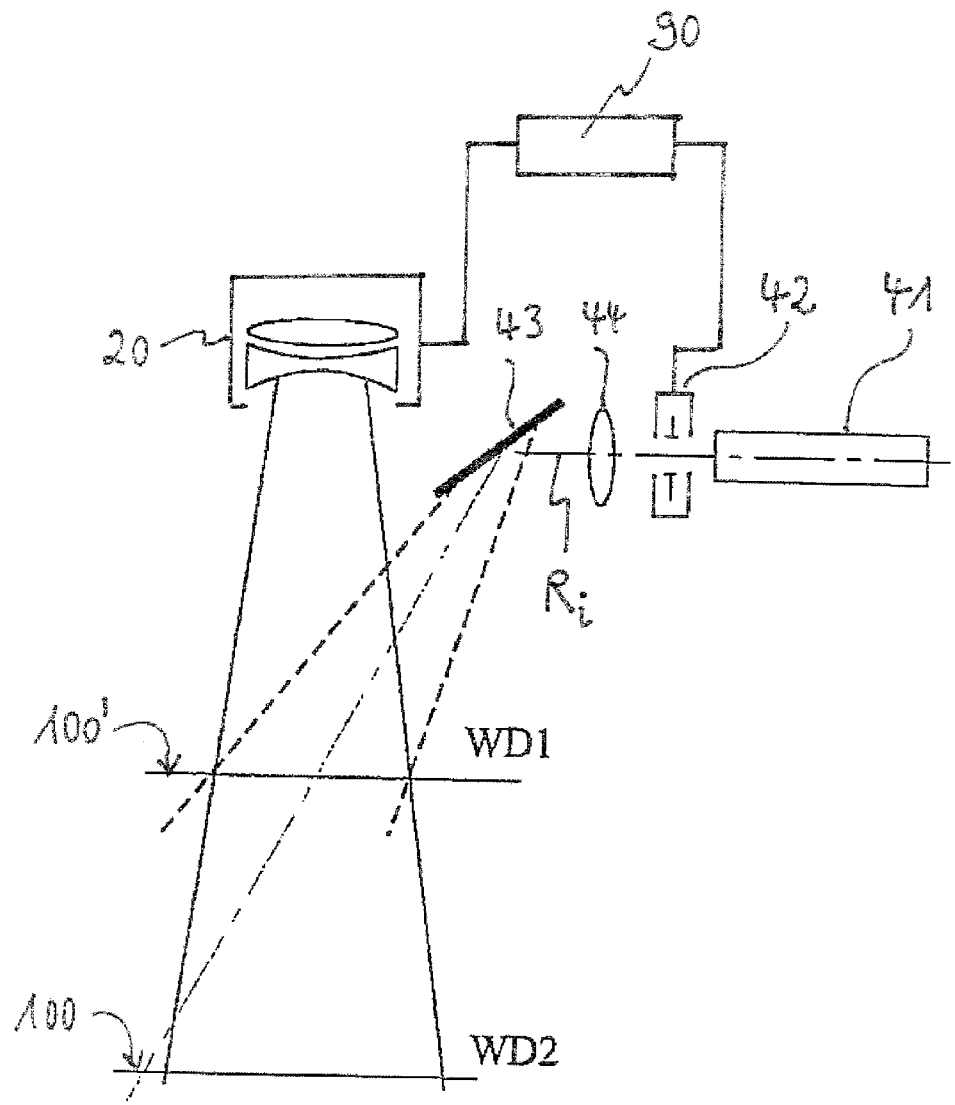
FIG. 3 schematically shows the inventive illumination centering given a second working distance, i.e. a second focal point of the main objective of the microscope.

FIG. 3 schematically represents a situation in which the focal length of the main objective 20 of the microscope 10 (see FIG. 1) is reduced compared to the focal length according to FIG. 2 so that the working distance decreases from WD2 to WD1. The angle θ (see FIG. 1) has to be correspondingly increased given a transition of the working distance from WD2 to WD1. According to the invention this is achieved by a lateral shift of the position of the field diaphragm 42. By means of such a lateral shift of the field diaphragm 42, the axis of the illuminating beam path directed onto the object plane 100 via the illumination deflector element 43 and thus the illuminated field can be laterally shifted in horizontal direction in the drawing plane.

It is advantageous when a control unit 90 is provided for the coupling of a variation of the focal length of the main objective 20 with the amount of lateral shift of the field diaphragm 42 of the illuminating unit 40. This control unit 90 is only schematically illustrated in FIGS. 2 and 3, a signal being supplied to the control unit 90 via an input thereof, which signal indicates a variation of the focal length of the main objective 20, and the respective required amount of shift of the field diaphragm 42 being output as a signal via an output of the control unit 90, which output signal controls in a manner know per se, for example, a stepper motor. The relationship between the amount of shift and the variation in focal length can practically be established in a simple way for example with the aid of known software by the so-called "ray tracing" and a best-fit method.

The possibilities of varying the focal length of a main objective 20 have already been mentioned in the introductory part of the specification. Common is the combination of a fixed and a movable lens for varying the focal length and the intercept length of the main objective. The movement of the movable lens can be measured directly and can be assigned to the varying intercept length of the main objective or its working distance. Altogether, the illumination centering according to the invention can thus be put into practice with known control methods.

As already mentioned, the shift of the field diaphragm 42 can, insofar as required, also have, in addition to a component perpendicular to the axis $R_i$ of the illuminating beam path, an axial component, i.e. parallel to this axis $R_i$. As already mentioned, it can be advantageous to image the field diaphragm 42 by means of an axial shift of the same with edge-sharpness on the object plane that has been assigned to the varied focal length of the main objective. In principle, a circular arc shift along a circular arc for example with the center on a point of the illuminating axis $R_i$ in the collector 41 is also conceivable. However, here it has to be taken into account that a coupling of the focal length variation of the main objective with a linear movement of the field diaphragm 42 can be realized in a technically easier way. In this connection, it is moreover pointed out once again that the deflector element 43 does not have to be tiltably mounted about an axis in the illumination centering according to the invention, i.e. can be stationary during the illumination centering.

FIG. 4 schematically shows a cutout of FIG. 3 and the lateral shift of the field diaphragm 42 required for this. Again illustrated are the collector 41, the field diaphragm 42 and the lens assembly 44 of the illuminating unit 40 of FIG. 3. The lateral shift, here perpendicular to the illuminating axis $R_i$ is designated with Δv. The shift Δv refers to the lateral shift with respect to an original position at which the geometric center of the field diaphragm 42 lies on the illuminating axis $R_i$. It can be taken from FIG. 4, that a small shift Δv of the field diaphragm 42 in upward direction is sufficient to center the illuminating beam path via the deflector element 43 optimally to the new working distance WD1 (see FIG. 3).

If required, further parameters of the illuminating unit can be optically varied in order to achieve an optimal coupling of the illuminated field with the field of view with respect to position, size and brightness. As an example, a variation of the intercept length of the lens assembly 44 is mentioned, as a result whereof the illumination intercept length can be adapted or tracked to the viewing intercept length. As a result, the intensity in the illuminated field is varied and can thus be optimally coupled with the varied focal length of the main objective 20. Further, the opening diameter of the field diaphragm 42 can be coupled with a variation of the working distance. As a result, the size of the illuminated field can be optimally adapted to the size of the field of view. For the purposed mentioned, the control unit 90 (see FIGS. 2 and 3) can comprise further outputs which are connected to corresponding adjustment devices for adjusting the lens assembly 44 and/or the opening diameter of the diaphragm 42.

For the purposes of completeness, it is still added that a shift Δv of the field diaphragm starting out from its normal position perpendicularly downwardly would result in a relative shift of the illuminating axis $R_i$ with respect to the viewing axis (optical axis of the main objective 20) in the opposite direction, i.e. starting out from FIG. 2 towards the right in the drawing plane. Such a shift would be necessary when the working distance would be increased to a working distance greater than WD2.

LIST OF REFERENCE NUMERALS 10 microscope
20 main objective
23 optical axis
30 zoom system
40 illuminating unit
41 collector
42 diaphragm, iris diaphragm, field diaphragm
43 illumination deflector element
44 lens assembly
50 deflector element
51 deflector element
52 deflector element
60 tube
70 eyepiece
80 light guide
90 control unit
100, 100' object plane
110 observer
I first horizontal plane
II second horizontal plane
$R_o$ viewing axis
$R_i$ illuminating axis
Δv lateral shift
θ angle $R_i$ to $R_o$

The invention claimed is:

1. A microscope comprising:
a main objective having a variable focal length;
an illuminating unit comprising an illuminating optical system for generating an illumination having an illuminating beam path directed onto an object plane and extending outside the main objective, wherein the illuminating optical system comprises a field diaphragm that is laterally shiftable for centering the illumination dependent on various focal lengths of the main objective and comprises an adjustable opening diameter; and
a control unit configured to control an amount of lateral shift and the opening diameter of the field diaphragm of the illuminating optical system dependent on an amount by that the focal length of the main objective has been varied.

2. The microscope according to claim 1, wherein the field diaphragm is axially shiftable.

3. The microscope according to claim 1, wherein the illuminating unit has as an illuminating optical system, a collector, the field diaphragm, an illumination deflector element as well as a lens assembly for focusing the illuminating beam path onto the object plane.

4. The microscope according to claim 3, wherein the illumination deflector element has a fixed position.

5. The microscope according to claim 1, wherein the microscope has a zoom system arranged downstream of the main objective as viewed from the object plane.

6. The microscope according to claim 5, wherein between the zoom system and the main objective a deflector element is arranged that directs the viewing beam path coming from the main objective into a first horizontal plane in that the longitudinal axis of the zoom system lies.

7. The microscope according to claim 6, wherein the microscope has a tube and an eyepiece, both being arranged downstream of the zoom system, wherein at least the tube is arranged with its longitudinal axis in a second horizontal plane that extends substantially parallel to the first horizontal plane.

8. The microscope according to claim 5, wherein the microscope has a tube and an eyepiece, both being arranged downstream of the zoom system.

9. The microscope according to claim 1, wherein the microscope is designed as a stereomicroscope.

10. The microscope according to claim 9, wherein the microscope is designed as a surgical microscope.

* * * * *